United States Patent [19]

Ramprasad et al.

[11] Patent Number: 5,895,823
[45] Date of Patent: Apr. 20, 1999

[54] PROCESS FOR THE PREPARATION OF AQUEOUS SOLUTIONS OF BETAINE

[75] Inventors: Dorai Ramprasad, Allentown; William Eamon Carroll, Orefield; Francis Joseph Waller, Allentown, all of Pa.

[73] Assignee: Air Products and Chemicals, Inc., Allentown, Pa.

[21] Appl. No.: 09/016,549

[22] Filed: Jan. 30, 1998

[51] Int. Cl.$^6$ .................................................. C07C 229/00
[52] U.S. Cl. ................................................................ 562/575
[58] Field of Search ...................................................... 562/575

[56] References Cited

U.S. PATENT DOCUMENTS

| | | | |
|---|---|---|---|
| 3,480,665 | 11/1969 | Nagy | 260/501.13 |
| 4,135,980 | 1/1979 | Ikuta et al. | 195/62 |
| 4,245,050 | 1/1981 | Nakanishi et al. | 435/191 |
| 4,497,825 | 2/1985 | Bade | 514/556 |
| 5,187,088 | 2/1993 | Furuoya et al. | 435/191 |
| 5,292,942 | 3/1994 | Aigner et al. | 562/575 |
| 5,684,191 | 11/1997 | Bellis et al. | 562/575 |

FOREIGN PATENT DOCUMENTS 50-96516  7/1975  Japan.

OTHER PUBLICATIONS

Mita, Y. "The Latest Technical Information Characteristics of the Betaine and its Application" *Gekkan Fudo Kemi Karu*, 7 (6), pp. 112–120; 1991.

Mallat, T., et al. "Oxidation of Alcohols With Molecular Oxygen on Platinum Metal Catalysts in Aqueous Solutions" *Catalysis Today*, 19, pp. 247–284; 1994.

*Kirk Othmer Encyclopedia of Chemical Technology*, vol. 6, p. 9.

*Primary Examiner*—Brian M. Burn
*Assistant Examiner*—Brian J. Davis
*Attorney, Agent, or Firm*—Mark L. Rodgers

[57] ABSTRACT

Betaine is produced by the oxidation of a choline salt in the presence of a supported noble metal catalyst at temperatures from about 20° C. to 100° C. and pressures from atmospheric to about 100 psi. This process is advantageous over prior processes for the production of betaine in that no amine halocarboxylate contaminants are produced by this reaction.

9 Claims, No Drawings

PROCESS FOR THE PREPARATION OF AQUEOUS SOLUTIONS OF BETAINE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention deals with a process to prepare aqueous solutions of betaine. This product is of value both as an animal feed and in the personal hygiene sector as a skin cleanser. The most common method for the preparation of betaine is by the reaction of trimethylamine with an alpha-halocarboxylic acid in the presence of an alkali metal hydroxide (for example see U.S. Pat. Nos. 4,497,825 and 5,292,942). There are several disadvantages to this method. For example, sodium chloride is always a co-product, and has to be removed(see U.S. Pat. No. 3,480,665). In addition to this, there is the concern of having the starting materials trimethylamine and halocarboxylate as contaminants, and the process has to be modified to achieve low levels of trimethylamine.

U.S. Pat. No. 5,684,191 teaches a method for the combined synthesis of betaine and choline chloride from monochloroacetic acid, trimethylamine and ethylene oxide by first reacting trimethylamine with monochloroacetic acid and then reacting ethylene oxide with the reaction product of the previous step. As with the previously described processes, contaminants from the reaction are a problem. Other synthetic methods for the production of betaine are described in Gekkan Fudo Kemi Karu (1991), 7(6), 112–20.

Another route to prepare betaine is by the oxidation of choline $[Me_3NCH_2CH_2OH]^+$ using oxygen and an enzyme choline oxidase(see U.S. Pat. Nos. 5,187,088, 4,245,050, and 4,135,980). The oxidation produces 2 moles of hydrogen peroxide for each mole of betaine produced. Consequently, this method is not used to manufacture betaine, but is useful as an analytical technique to detect choline by measuring the generated hydrogen peroxide.

The oxidation of primary alcohols to the carboxylic acid salts using alkali metal hydroxide in the presence of precious metals such as Pd, Pt, Rh, Ru, Ir, Os, Re is well known(see Catalysis Today 19 (1994), 247–284). Japanese Patent No 50-96516A discloses a process for the preparation of carboxylic acid salts by the liquid phase dehydrogenation of alcohols with caustic alkali in the presence of precious metals such as Pd. This process uses a high temperature, 100° C.–270° C., and uses alcohols such as diethylene glycol. The inherent disadvantage in this process is that high temperatures ≧ 100° C. must be used and that the alkali metal salt of the desired acid is produced. There is literature, see Kirk Othmer Encyclopedia of Chemical Technology, Vol. 6, p 9, showing concentrated solutions of choline as the free base decompose at 100° C. to give trimethylamine ethylene glycol and poly(ethylene glycol). Therefore one skilled in the art would expect such a molecule to degrade under the conditions of oxidation, high temperatures and alkaline solutions.

BRIEF SUMMARY OF THE INVENTION

We have found that aqueous solutions of betaines can be prepared by reacting aqueous solutions of choline salts with oxygen in the presence of a supported noble metal catalyst. As used herein, betaines refer to compounds represented by the chemical formula $R_3N^+CH_2CO_2$— wherein each R is independently H or a $C_1$–$C_4$ alkyl group. The process is suitable for either batch or continuous reactor operation using temperatures from about 20° C. to 100° C. and pressures from atmospheric up to about 100 psi.

DETAILED DESCRIPTION OF THE INVENTION

The compound choline is a commercially available material and is sold in aqueous solutions in salt form. We have found that aqueous choline salts in the presence of a supported noble metal catalyst can be partially oxidized to form aqueous mixtures of betaine/choline, or completely oxidized to betaine. The general reaction can be illustrated by the following chemical equation.

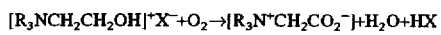

where each R is independently H or a $C_1$–$C_4$ alkyl group, and $X^-$ is any anion capable of forming a salt with the choline cation. Examples of suitable anions include $OH^-$, $R'CO_2^-$ ($R'$=H, alkyl, haloalkyl, aryl or haloaryl), $SO_4^=$, $NO_3^-$, $CO_3^=$, $HCO_3^-$, $HSO_4^-$, $HSO_3^-$, $PF_6^-$, $BF_4^-$, $CF_3CO_2^-$, $ClO_4^-$, $CF_3SO_3^-Cl^-$, $BF^-$, $I^-$, $F^-$, and $C_4H_5O_6^-$. In the case of many of these anions, additional base such as NaOH must be added to make the solution alkaline for the oxidation to proceed. In the case where $X^-=OH^-$ or the anion of a weak acid such as acetate or bicarbonate, no additional base is necessary, although additional base may enhance the reaction rate.

The advantages of this process over the prior art processes for the production of betaine compounds are that no amine halocarboxylate contaminants are produced and no $H_2O_2$ is generated as in the biochemical method. Additionally, when choline salts which do not require added base are used, such as choline hydroxide, choline acetate or choline bicarbonate, no alkali metal salts are generated.

Though the use of other choline salts may require added base and therefore produce alkali metal salt byproducts, the reaction still offers an advantage over the traditional method of reacting trimethylamine, chloroacetic acid and a base, in which case trimethylamine and chloroacetate contamination is a problem in addition to salt removal. Surprisingly, for the most part, we have found that the anions ($X^-$) do not poison the catalyst under reaction conditions, except that at high concentrations, i.e., greater than about 40%, some anions, such as $Cl^-$, begin to show a detrimental effect.

In summary, we have found that aqueous solutions of choline salts can be oxidized to betaine at temperatures from about 20° C. to 100° C. with high conversion and/or selectivity using oxygen at pressures from atmospheric to about 100 psi and a supported heterogeneous catalyst. The supported heterogeneous catalyst comprises a noble metal on a suitable support. The choline/noble metal molar ratio can vary between about 10 and 500. The examples that follow demonstrate the use of Pd/C and Pt/C, although other noble metal catalysts such as Rh, Ru, Ir, and Re can also be used. Any support which is stable and inert to reaction conditions, such as carbons, can be used, and promoters such as Cd, Bi, or Pb may also be added. The claimed process is suitable for either batch or continuous reactor operation using temperatures up to 100° C. and oxygen pressures up to 100 psi.

Depending upon the end use and economics involved, it may be desirable to only oxidize a portion of the choline to produce an aqueous mixture of choline/betaine, or alternatively, complete oxidation of the choline to betaine may be desired. By adjusting the parameters, such as type of catalyst, catalyst concentration, anion, choline concentration, reaction time, the amount of choline oxidation can be controlled.

The following examples are presented to better illustrate the present invention and are not meant to be limiting.

EXPERIMENTAL SECTION

All experiments were carried out in a three necked glass flask equipped with an oxygen bubbler, water cooled condenser, and a thermometer. The flask was heated via a heating mantle connected to a thermal watch to maintain temperature. The aqueous solutions were stirred with a magnetic stirrer. The amount of betaine and choline were calculated from their relative integrations in the $^{13}C$ NMR spectrum.

EXAMPLE 1

Oxidation of Choline Chloride to Betaine at Two Different Temperatures

Into a three necked flask was added 23.5 g of a 70% choline chloride solution followed by 300 ml of deionized water. To this was added 8.6 g of NaOH, followed by 3.3 g of a 5% Pt/C catalyst. The solution was sparged with oxygen and heated at 75° C. for 4 hours, and then filtered and analyzed by $^{13}C$ NMR. The experiment was repeated at room temperature for 18 hours and the results are compared below.

| Temperature ° C. | Time (hrs) | Choline Conversion % | Betaine Selectivity % |
| --- | --- | --- | --- |
| 25 | 18 | 7 | ~100 |
| 75 | 4 | 35 | 85 |

The results show that the room temperature oxidation is slow compared to that at higher temperature, although both reactions exhibited high selectivity to betaine.

EXAMPLE 2

Comparison of Choline Hydroxide Oxidation Versus Choline Chloride

To a three necked flask was added 200 ml of deionized water followed by 2.1 g of a 5% Pt/C catalyst. To this was added 25 ml of a 50% choline hydroxide solution (Aldrich), and the mixture was sparged with oxygen, stirred and heated at 78° C. for 3 hours, then filtered and analyzed. The experiment was repeated with 15.45 g of choline chloride dissolved in 275 ml of water to which 4.4 g of NaOH was added. The results are shown below.

| Sample | Catalyst (gm) | Choline Conversion % | Betaine Selectivity % |
| --- | --- | --- | --- |
| choline hydroxide | 5% Pt/C, (2.1) | 14.2 | 70 |
| choline chloride | 5% Pt/C (2.1) | 17.5 | 60 |

The results show that the oxidation proceeds similarly with both the hydroxide and chloride.

EXAMPLE 3

Oxidation Using Different Amounts of PD/C Catalyst Using Dilute Solutions, ~6% by weight Approximately 15.5 g of choline chloride was dissolved in 275 ml of water. To this was added 4.4 g of NaOH followed by 4.2 g of 5% Pd/C. Oxygen was sparged through the mixture with stirring for 3 hours at 78° C., after which the solution was filtered and analyzed. The experiment was repeated with different amounts of catalyst and the results are shown below.

| Weight of Catalyst (g) | Choline/Pd Molar Ratio | Choline Conversion % | Betaine Selectivity % |
| --- | --- | --- | --- |
| 2.1 | 113 | 33 | 60 |
| 4.2 | 56 | 28 | 63 |
| 6.3 | 38 | 47 | 83 |
| 10 | 24 | 55 | 73 |

The results show that that though there is no linear increase of conversion versus amount of catalyst, there is a general trend of more conversion with more catalyst.

EXAMPLE 4

Reaction to Prepare Betaine with High Conversion and Selectivity Using a 14% Choline Chloride Solution To 100 ml of water was added 15.5 g of choline chloride, followed by 4.5 g of NaOH and 10 g of a 5% Pd/C catalyst. Oxygen was sparged through the solution for 5.5 hours at 78° C., which was then filtered and analyzed. The results are shown below.

| Weight of Catalyst (g) | Choline/Pd Molar Ratio | Choline Conversion % | Betaine Selectivity % |
| --- | --- | --- | --- |
| 10 | 24 | 88 | 85 |

EXAMPLE 5

Reaction to Prepare Betaine Using High Concentrations (40%) of Choline Chloride or Hydroxide To 100 ml of water was added 50 g of choline chloride, followed by 14.3 g of NaOH and 10 of a 5% Pd/C catalyst. Oxygen was sparged through the solution for 5.5 hours at 78° C., which was then filtered and analyzed. The experiment was repeated with a solution prepared with 81 ml of choline hydroxide to which 10 ml of water was added, followed by 10 g of a 5% Pd/C. The results are shown in the table that follows.

| Sample | Choline/Pd Molar Ratio | Choline Conversion % | Betaine Selectivity % |
| --- | --- | --- | --- |
| choline chloride | 76 | 28 | 72 |
| choline hydroxide | 76 | 89 | 87 |

The results show that choline hydroxide works better than chloride at high concentrations showing that chloride could be a poison at higher concentration.

EXAMPLE 6

Reaction to Prepare Betaine Using a High Concentration (47%) Solution of Choline Bicarbonate Approximately 63 ml of a 75% choline bicarbonate was diluted with 42 ml of water and then mixed with 10 g of a 5% Pd/C. Oxygen was sparged for 5 hours at 78° C. after which product was filtered and analyzed. The result is shown below.

| Sample | Choline/Pd Molar Ratio | Choline Conversion % | Betaine Selectivity % |
|---|---|---|---|
| choline bicarbonate | 76 | 14 | 85 |

Result shows that bicarbonate is not as good as hydroxide.

Having thus described the present invention, what is now deemed appropriate for Letters Patent is set out in the following appended claims.

We claim:

1. A process for preparing aqueous solutions of betaines which comprises reacting an aqueous solution of choline hydroxide with oxygen in the presence of a supported noble metal catalyst at a temperature from about 20° C. to 100° C.

2. A process in accordance with claim 1 which is carried out at a pressure from about atmospheric to 100 psi.

3. A process in accordance with claim 1 wherein said choline hydroxide is represented by the structural formula:

[R$_3$NCH$_2$CH$_2$OH]$^+$X$^-$ wherein each R is independently H or a $C_1$ to $C_4$ alkyl group; and X$^-$ is OH$^-$.

4. A process in accordance with claim 1 wherein said betaines are represented by the structural formula:

R$_3$N$^+$CH$_2$CO$_2$$^-$ wherein each R is independently H or a $C_1$ to $C_4$ alkyl group.

5. A process in accordance with claim 1 wherein said catalyst comprises Pt or Pd on a support.

6. A process in accordance with claim 5 wherein said catalyst support is carbon.

7. A process in accordance with claim 1 wherein a promoter is added to the reaction.

8. A process in accordance with claim 7 wherein said promoter is Cd, Bi or Pb.

9. A process in accordance with claim 1 wherein the choline/noble metal molar ratio is from 10 to 500.

* * * * *